United States Patent [19]
Lin et al.

[11] Patent Number: 5,770,761
[45] Date of Patent: Jun. 23, 1998

[54] PROCESS FOR ETHYL ACETATE PRODUCTION

[75] Inventors: Tzong-Bin Lin, Chia-Yi, Taiwan; Karl T. Chuang, Alberta, Canada; Kun-Yung Tsai, Tao-Yuan; Jen-Ray Chang, Chia-Yi, both of Taiwan

[73] Assignee: Chinese Petroleum Corporation, Taipei, Taiwan

[21] Appl. No.: 744,880

[22] Filed: Nov. 8, 1996

[51] Int. Cl.$^6$ ................................................. C07C 69/02
[52] U.S. Cl. ............................................................. 560/231
[58] Field of Search ............................................ 560/231

[56] References Cited

U.S. PATENT DOCUMENTS

| | | | |
|---|---|---|---|
| 4,275,228 | 6/1981 | Gruffaz et al. | 560/247 |
| 4,313,960 | 2/1982 | Campagne | 426/17 |
| 4,780,566 | 10/1988 | Braca et al. | 560/265 |
| 4,886,905 | 12/1989 | Larkins, Jr. | 560/265 |
| 5,009,872 | 4/1991 | Chuang et al. | 423/245.3 |
| 5,241,106 | 8/1993 | Inoue et al. | 560/247 |
| 5,334,751 | 8/1994 | Lemanski et al. | 560/265 |

FOREIGN PATENT DOCUMENTS 355022640  2/1980  Japan .

*Primary Examiner*—Porfirio Nazario-Gonzalez
*Assistant Examiner*—Rosalynd Keys
*Attorney, Agent, or Firm*—Burns, Doane, Swecker and Mathis

[57] ABSTRACT

Oxidation of liquid ethanol in the presence of excess liquid ethanol and a supported oxidation catalyst provides a one step process for production of ethyl acetate. The acetic acid produced in the oxidation is absorbed by the excess liquid ethanol, which esterifies to ethyl acetate. Ethyl acetate and water are removed from the process for separation of the ethyl acetate. The oxidation portion of process is preferred with a metallic oxidation catalyst on a hydrophobic support. The esterification portion of the process is preferred with an acidic solid ion exchange resin to promote the esterification. The process can be performed in series in separate steps, or preferably, in parallel in a single vessel, preferably a trickle bed reactor.

18 Claims, 1 Drawing Sheet

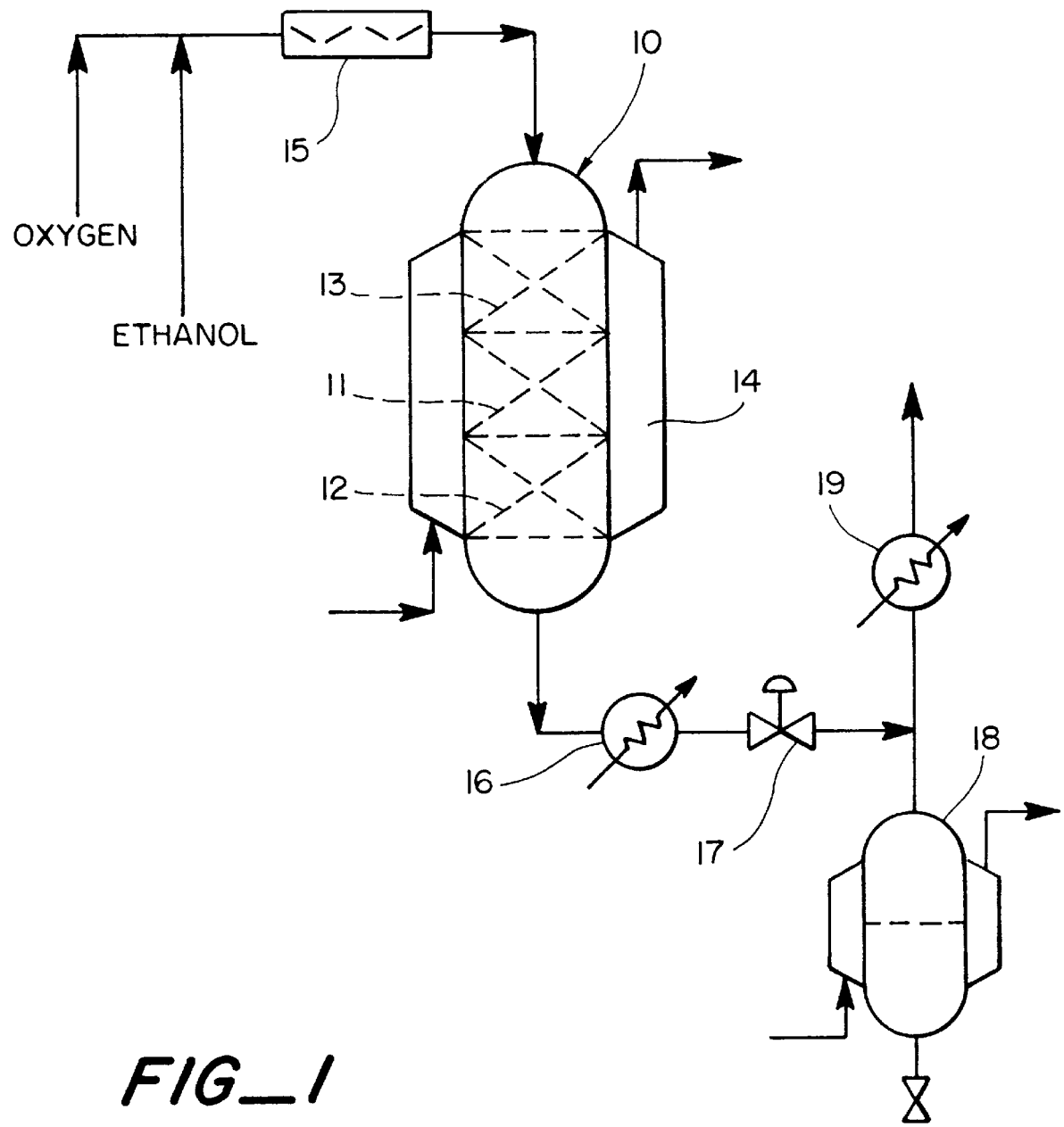
FIG_1

PROCESS FOR ETHYL ACETATE PRODUCTION

FIELD OF THE INVENTION

This invention relates to a process for the conversion of ethanol to ethyl acetate.

Ethyl acetate is mainly used as a solvent in the paint and coatings industry. It is a very useful chemical which has valuable solvent properties. Its physiologic harmlessness in combination with its oleophilic character has made it especially suitable for extraction processes in the food industry and for the preparation of cosmetics. Its low boiling point is the basis for its application as a high grade defatting agent. The high standard purity of the commercial product accounts for its use as an anhydrous reaction medium and also as an intermediate in chemical syntheses.

BACKGROUND OF THE INVENTION

The commercial production of ethyl acetate is mainly by two processes: the Tischenko reaction produces ethyl acetate by direct conversion of ethanol via acetaldehyde using an aluminum alkoxide catalyst; and the production of ethyl acetate by direct esterification of ethanol with acetic acid with a sulphuric acid catalyst. The Tischenko reaction is the main industrial process for the manufacture of ethyl acetate. Industrial scale production by this method took place mainly in Europe during the first half of this century. Ethyl acetate is also produced as a by-product in the liquid phase oxidation of n-butane and as a co-product in the production of polyvinyl butyryl from vinyl acetate and ethanol.

In the Hoechst process, a catalyst solution of aluminum ethoxide is first prepared by dissolving granular aluminum in an ethanol-ethyl acetate mixture in the presence of aluminum chloride and a small amount of zinc chloride. The reaction evolves hydrogen and is exothermic. Intensive cooling is required to prevent the loss of organic matter. The final solution contains about 2% aluminum. The next step in the process is to introduce the catalyst solution along with acetaldehyde simultaneously into a reactor. The reaction varies according to the temperature and the catalyst quantity. These parameters are adjusted to accomplish about 98% conversion in one pass through the reactor. A further 1.5% transformation is obtained in the stirring vessels where a residue is separated from the product. The reactor is kept cooled to about 0° C. by the use of a chilled brine. The residence time in the reactor is about one hour.

The distillable products are removed in the residue separation vessel by evaporation. The residue is treated with water to convert as much as possible to ethanol. The remainder can either be treated in a biological degradation plant or incinerated. The combined distillable products are then separated in a series of distillation steps to give ethyl acetate, the product; unconverted acetaldehyde, for recycle; light ends which can be used for fuel; a mixture of ethyl acetate and ethanol, which can be used in the catalyst preparation step; and a by-product, acetaldehyde diethyl acetal, which can be recovered for sale or hydrolyzed for recovery of acetaldehyde and ethanol.

In the esterification process, ethanol and acetic acid are combined with a recycle of crude ethyl acetate in a reactor which is also an azeotropic distillation column. The reaction produces water as a waste product. The water impedes the reaction, and the reaction column removes the water as an azeotrope as it is generated. The overhead condensate is collected in a decanter where the product separates into two phases. The organic phase is partially recycled to the reaction column and the balance is fed to a second distillation column which produces a bottoms product of ethyl acetate and an overhead product of an azeotrope of ethyl acetate, water and ethanol. The overhead condensate is collected in a second decanter, where it separates into two phases as before. The organic phase is recycled to the column while the aqueous phase is combined with the aqueous phase from the first column and fed to a third column to produce a wastewater stream from the bottom and the azeotrope from the top. The azeotrope is recycled to the reaction column.

In another process ethyl acetate is synthesized from ethylene and acetic acid. This method claims ecological benefits in that it produces less wastes than the aluminum chloride catalyzed process. In this process, disclosed in U.S. Pat. No. 4,275,228, ethyl acetate is prepared by the vapor phase reaction of ethylene and acetic acid utilizing as a solid catalyst ion exchange fluoropolymer comprising sulfonic acid moieties. The feed usually has an excess of ethylene. Conversions of acetic acid vary from 30% with a residence time of 55 hours at 126° C. to 60% with a residence time of 30 hours at 150° C. As a consequence of this slow reaction-rate, the process requires an extremely large reactor size.

U.S. Pat. No. 5,241,106 reveals a variation on the process whereby the catalyst comprises tungstophosphoric acid of which 10–90% of the total amount of proton is replaced by a cesium cation or a combination of a cesium cation plus at least one cation from alkali metal cations other than cesium or a combination of a cesium cation plus at least one cation of iron group metal cations. This process can produce ethyl acetate by either a vapor phase reaction or a liquid phase reaction and the reaction rate can be improved by the addition of water to the feed. The reaction times are significantly shortened, but they are still longer than desired.

U.S. Pat. No. 4,886,905 describes another approach based on acetic anhydride as the feed material. The acetic anhydride is hydrogenated at elevated temperatures and pressures in the presence of a homogeneous ruthenium catalyst, methyl iodide and, optionally, lithium iodide. The process produces either ethyl acetate or ethylidene diacetate or both, depending on reaction conditions. This process can provide high reaction rates, but the process is complex. Acetic acid is produced as a co-product, which must be separated and converted back to acetic anhydride, and the process requires the availability of hydrogen at high pressure. The catalyst and iodides must be removed from the reaction products and recycled.

U.S. Pat. No. 4,780,566 describes another approach based on methyl acetate. The methyl acetate, either alone or in a mixture with acetic acid in the presence of a ruthenium compound and a promotor of hard acid type in an atmosphere of hydrogen and carbon dioxide produces ethyl acetate and acetic acid. This process is also complex and provides poor selectivity. In addition to acetic acid, alcohols, ethers, propionates, methane and ethane are co-produced significant quantities.

There is a need in the industry for a more efficient process for the production of ethyl acetate.

The disclosures of the above patents are incorporated herein by reference.

SUMMARY OF THE INVENTION

The present invention provides a single step, single vessel conversion of ethanol to ethyl acetate. The first part of the process is the partial oxidation of part of the ethanol to acetic acid by oxygen (or air), and the second part is the esterification of the acetic acid with a second part of the ethanol.

The first reaction is catalyzed by a palladium type catalyst, while the second reaction proceeds spontaneously or can be catalyzed by a solid ion exchange resin in the acid form. The catalysts can be mixed so that the reactions proceed in parallel, or separated so that the reactions proceed sequentially.

The products of reaction are limited to ethyl acetate, acetic acid, acetaldehyde and water. The feed ethanol can be either pure ethanol or commercial ethanol (constant boiling or lower purity).

The reaction system is well suited for a trickle bed catalytic type process. Because water is present, the oxidation reaction is enhanced if the oxidation catalyst, Pd, is supported on a hydrophobic carrier.

Thus, a single step, single vessel process for the conversion of ethanol to acetic acid is provided, comprising reacting the alcohol with oxygen or air in the presence of a noble metal oxidation catalyst preferably on a hydrophobic support with excess liquid ethanol present as a solvent to absorb the acetic acid as it forms. The acetic acid formed reacts with the liquid ethanol to form ethyl acetate. The esterification reaction proceeds spontaneously and in parallel with the oxidation reaction, but reaches equilibrium concentrations more rapidly in the presence of an acid catalyst, such as a solid ion exchange resin for example Amerlyst 15 in the acid form.

BRIEF DESCRIPTION OF THE DRAWING

The FIGURE is a schematic diagram of a typical apparatus used to carry out the process of this invention.

DESCRIPTION OF THE INVENTION

The experimental proofs of the concept were conducted in an apparatus of the type illustrated in the FIGURE. As seen in FIG. 1, a pressurized packed trickle bed reactor 10 made from type 316 stainless steel contains the catalyst(s) 11. The reactor volume was approximately 80 cc's. The catalyst(s) were supported on glass beads 12. The reactants were distributed over the catalysts by another layer of glass beads 13 at the top of the bed.

The oxidation catalyst was an oxidation catalyst containing a noble metal (Pt, Pd, Rh, or Ir) or combinations thereof, on a hydrophobic support, e.g. styrene-divinylbenzene co-polymer, fluorinated carbon and silicalite or on activated carbon. See U.S. Pat. No. 5,009,872, the disclosure of which is incorporated herein by reference. The surface area should be high enough so that sufficient metal catalyst can be deposited with good dispersion, say in the range of 50–800 square meters per gram.

The solid acid catalyst can be a solid ion exchange resin in the acid form. Specifically, Amberlyst 15 in the acid form has been found to be effective.

The bed packing was a mixture of the catalyst and an inert support. In the case where the reaction proceeds in parallel, the oxidation catalyst and the solid acid catalyst were blended together with glass beads and placed on a bed of sized glass beads. Layers of sized glass beads were then placed on top of the catalyst bed and the reactor was closed.

In the case where the reactions ~ proceeded sequentially, the solid acid catalyst mixed with glass beads was placed on a bed of sized glass beads, a layer of glass beads was placed on top of the catalyst and bed of oxidation catalyst mixed with glass beads was placed on top of the separating layer of glass beads. Finally, a layer of glass beads was placed on top of the hydrophobic catalyst and the reactor was closed.

The reactor was then placed inside a heating jacket 14 to control the reaction temperature. A heat transfer liquid was circulated through the jacket in series with a constant temperature bath to maintain the reactor temperature.

Temperatures in the range of from 75° to 150° C. are contemplated.

Pressures ranging from 20 bar to 40 bar are suitable.

The use of liquid ethanol in the trickle bed reactor enhances the process in two ways:

1) it rapidly removes the exothermic heat of reaction, thus reducing the probability of hot spots 2) it keeps the catalyst surface clean, ensuring high reaction rates.

In operation, liquid ethanol and compressed oxygen were metered into the reactor using mass flow controllers. The reactants passed through a static mixer 15 prior to entering at the top of the reactor. The reactants flowed concurrently downward to avoid flooding the reactor. The acetic acid formed was absorbed by the excess ethanol and reacted with it to produce ethyl acetate and water.

The reactor effluent containing ethyl acetate and water was removed from reactor 10 and cooled by heat exchange in a cooler 16 using a circulating coolant. The pressure of the system was controlled using a back pressure regulator 17 which regulated the flow out of the reactor. The cooled effluent then passed into a receiver 18 chilled by circulating coolant where the liquid separated from the vapor. The vapor stream passed through a condenser 19 which condensed vapors from the spent air stream. The condensed vapors flowed by gravity into the receiver.

In the cases where the reactions proceeded in parallel, the catalyst bed comprised 2 grams of 10%PD/SDB hydrophobic catalyst or 10% Pd/C catalyst plus 2 grams of Amberlyst 15 mixed with 15 cc's of glass beads. This bed rested on 15 cc's of 0.2–0.4 mm glass beads on top of 10 cc's of 2 mm glass beads. At the top of the catalyst bed was a layer of 15 cc's of 0.2–0.4 mm glass beds covered by a layer of 10 cc's of 2 mm glass beads.

In the cases were the reactions proceeded sequentially, the reactor was filled with 10 cc's of 2 mm glass beads at the bottom followed by 10 cc's of 0.2–D.4 mm glass beads followed by 10 cc's of a mixture of 2 grams of Amberlyst 15 in 10 cc's of glass beads followed by a layer of glass beads and then a layer of a mixture of 10% Pd/SDB hydrophobic catalyst or 10% Pd/C catalyst in 10 cc's of glass beads covered by a layer of sized glass beads as in the previous example.

A series of examples were also run without the use of the solid acid catalyst to demonstrate that the esterification reaction will proceed in the reactor without the use of a catalyst. In this case, the catalyst bed was prepared as described previously but with a catalyst bed comprising 2 grams of 10% Pd/SDB mixed with glass beads without the solid acid catalyst.

Other tests were run with the Pd dispersed onto a carbon carrier to demonstrate the benefits of a hydrophobic carrier. In this case, the reaction occurred, but more slowly.

Another set of tests were run comparing the effectiveness of the oxidation catalyst when the palladium is oxidized to the more normal case when the palladium is in the reduced state. Conversions to ethyl acetate were found to be higher when the palladium was in the oxidized state.

The ethanol fed to the reactor was either 93% ethanol or 99+% ethanol. Oxygen or air was metered into the reactor in a ratio of liquid ethanol to oxygen or air of 0.4 cc's 228 cc.

The following tables summarize the results of the tests:

Mixed Catalyst Bed-10% Pd/SDB and Amberlyst 15

WHSV H$^{-1}$ P(bar) T(° C.) % H$_2$O % CH$_3$CHO % C$_2$H$_5$OH % CH$_3$COOC$_2$H$_5$ % CH$_3$COOH (Ethanol Feed Purity=93.47%)

| | | | | | | | |
|---|---|---|---|---|---|---|---|
| 9.6 | 35.9 | 95 | 16.902 | 1.025 | 59.237 | 14.538 | 9.298 |
| 7.2 | 35.9 | 95 | 17.464 | 0.905 | 54.189 | 18.706 | 8.736 |
| 4.8 | 35.9 | 95 | 18.841 | 0.699 | 49.191 | 22.062 | 9.207 |
| 2.4 | 35.9 | 95 | 20.227 | 0.336 | 43.501 | 24.838 | 11.098 |
| 9.6 | 40.0 | 95 | 16.929 | 1.004 | 56.398 | 16.694 | 8.975 |
| 9.6 | 27.6 | 95 | 15.757 | 1.002 | 62.395 | 13.754 | 7.122 |
| 9.6 | 20.7 | 95 | 15.006 | 1.029 | 66.698 | 11.588 | 5.669 |
| 9.6 | 35.9 | 90 | 16.292 | 1.113 | 60.203 | 13.089 | 9.303 |
| 9.6 | 35.9 | 85 | 15.357 | 1.152 | 63.791 | 11.435 | 8.265 |
| 9.6 | 35.9 | 75 | 14.231 | 1.347 | 69.545 | 8.049 | 8.828 |

(Ethanol Feed Purity=99+%)

| | | | | | | | |
|---|---|---|---|---|---|---|---|
| 9.6 | 35.9 | 95 | 11.485 | 0.893 | 60.258 | 19.222 | 8.142 |

Single Catalyst Bed-10% Pd/SDB (Ethanol Feed Purity 93.47%)

| | | | | | | | |
|---|---|---|---|---|---|---|---|
| 9.6 | 35.9 | 95 | 17.152 | 0.243 | 62.708 | 10.722 | 9.175 |
| 7.2 | 35.9 | 95 | 17.968 | 0.329 | 53.653 | 14.929 | 13.121 |
| 4.8 | 35.9 | 95 | 19.653 | 0.204 | 48.573 | 17.242 | 14.328 |
| 2.4 | 35.9 | 95 | 21.642 | 0.049 | 40.425 | 21.224 | 16.661 |

(Ethanol Feed Purity=99+%)

| | | | | | | | |
|---|---|---|---|---|---|---|---|
| 9.6 | 35.9 | 95 | 12.586 | 0.557 | 58.270 | 18.091 | 10.496 |
| 7.2 | 35.9 | 95 | 13.427 | 0.401 | 52.345 | 20.995 | 12.832 |
| 4 8 | 35.9 | 95 | 13.897 | 0.216 | 49.655 | 22.346 | 13.886 |
| 2.4 | 35.9 | 95 | 14.310 | 0.118 | 48.704 | 22.718 | 14.150 |

Separate Catalyst Beds-10% Pd/SDB and Amberlyst 15

(Ethanol Feed Purity=93.47%)

| | | | | | | | |
|---|---|---|---|---|---|---|---|
| 9.6 | 35.9 | 95 | 18.443 | 0.627 | 52.074 | 20.228 | 8.628 |
| 7.2 | 35.9 | 95 | 19.258 | 0.549 | 48.207 | 22.614 | 9.372 |
| 4.8 | 35.9 | 95 | 20.537 | 0.353 | 43.027 | 25.391 | 10.692 |
| 2.4 | 35.9 | 95 | 21.774 | 0.158 | 38.287 | 22.619 | 11.962 |

(Ethanol Feed Purity=99+%)

| | | | | | | | |
|---|---|---|---|---|---|---|---|
| 9.6 | 35.9 | 95 | 12.556 | 0.820 | 59.130 | 21.630 | 5.864 |
| 7.2 | 35.9 | 95 | 14.143 | 0.592 | 51.438 | 25.962 | 7.865 |
| 4.8 | 35.9 | 95 | 15.294 | 0.405 | 46.858 | 28.555 | 8.889 |
| 2.4 | 35.9 | 95 | 16.351 | 0.207 | 42.709 | 30.911 | 9.822 |

Single Catalyst Bed-10% Pd on SDB and Carbon, Compared 10% Pd/SDB 10% Pd/C

| | | |
|---|---|---|
| Pressure, bar | 35.9 | 35.9 |
| WHSVh$^{-1}$ | 2.4 | 2.4 |
| Ethanol, % | 99+% | 99+% |
| Temperature °C. | 95 | 95 |
| Water, % | 14.281 | 13.564 |
| CH$_3$CHO, % | 0.117 | 1.038 |
| C$_2$H$_5$OH, % | 48.565 | 53.134 |
| CH$_3$COOC$_2$H$_5$, % | 23.066 | 19.060 |
| CH$_3$COOH, % | 13.950 | 13.204 |
| Ethanol, % | 93.47 | 93.47 |
| Water, % | 22.043 | 16.443 |
| CH$_3$CHO, % | 0.051 | 1.234 |
| C$_2$H$_5$OH, % | 40.820 | 58.532 |
| CH$_3$COOC$_2$H$_5$, % | 20.688 | 13.297 |
| CH$_3$COOH, % | 16.398 | 14.495 |

Single Catalyst Bed-10% Pd/SDB Pd Oxidized Comparison

| Catalyst | Pd/SDB | PdO/SDB | Pd/SDB | PdO/SDB | Pd/SDB | PdO/SDB | Pd/SDB | PdO/SDB |
|---|---|---|---|---|---|---|---|---|
| WHSV h$^{-1}$ | 9.6 | 9.6 | 7.2 | 7.2 | 4.8 | 4.8 | 2.4 | 2.4 |
| Ethanol, % | 93.47 | 93.47 | 93.47 | 94.47 | 93.47 | 93.47 | 93.47 | 93.47 |
| Water, % | 17.152 | 18.174 | 17.968 | 19.331 | 19.653 | 21.290 | 21.641 | 27.560 |
| CH$_3$CHO, % | 0.243 | 0.533 | 0.329 | 0.256 | 0.204 | 0.464 | 0.049 | 0.650 |
| C$_2$H$_5$OH, % | 62.708 | 57.640 | 53.653 | 47.970 | 48.573 | 41.907 | 40.425 | 32.585 |
| CH$_3$COOC$_2$H$_5$, % | 10.722 | 12.400 | 14.929 | 17.130 | 17.242 | 19.450 | 21.224 | 24.538 |
| CH$_3$COOH, % | 9.175 | 11.253 | 13.121 | 14.929 | 14.328 | 16.889 | 16.661 | 15.071 |
| Ethanol, % | 99+ | 99+% | 99+% | 99+% | 99+% | 99+% | 99+% | 99+% |
| Water, % | 12.586 | 13.120 | 13.427 | 13.892 | 13.897 | 17.319 | 14.310 | 22.464 |
| CH$_3$CHO, % | 0.557 | 0.881 | 0.401 | 0.555 | 0.216 | 0.439 | 0.118 | 0.245 |
| C$_2$H$_5$OH, % | 58.270 | 57.023 | 52.345 | 52.564 | 49.655 | 40.672 | 48.704 | 29.171 |
| CH$_3$COOC$_2$H$_5$, % | 18.091 | 17.584 | 20.995 | 20.702 | 22.346 | 24.757 | 22.718 | 30.891 |
| CH$_3$COOH, % | 10.496 | 11.393 | 12.832 | 12.287 | 13.886 | 16.783 | 14.150 | 17.229 |

It is postulated that when conventional catalyst is exposed to aqueous solutions, capillary condensation takes place until it reaches thermodynamic equilibrium dictated by the Kelvin equation $$\ln(P/P_o) = 2V \mu \text{ cps } \Theta/(rRT)$$

where r is the radius of the capillary, V is the molar volume of the liquid and $\mu$ is the surface tension. Equation (1) indicates that for values of the contact angle 0 less than 90 degrees, liquid condenses in the capillary at a pressure P less than the saturated pressure $P_o$ at temperature T. For conventional catalyst supports, the materials are hydrophilic and the contact angle with an aqueous solution would be close to zero. Thus the whole catalyst is wet when exposed to the liquid. The equation also implies that increasing contact angle reduces pore condensation. In the presence of a liquid, P is equal to $P_o$ and if a hydrophobic material with greater than 90 degrees (cos $\ominus$ becomes negative) is selected as a catalyst support, its pores will remain dry and accessible to the gaseous reactants. In this way, the concentration of the reactants at the reaction sites in the pores is increased by a factor of 10 to the 4th power, roughly the Henry's law constant for oxygen. In addition, the rate of diffusion in the gas phase is about 1,000 to 10,000 times higher than that in the liquid phase. Accordingly, the combination of carrying out the oxidation in the vapor phase and using a hydrophobic catalyst can be employed to increase reaction rates.

we claim:

1. A process for the production of ethyl acetate from ethanol by oxidation of ethanol characterized by:

contacting excess liquid ethanol with oxygen in the presence of a metallic oxidation catalyst to form acetic acid and in the presence of excess liquid ethanol to absorb the acetic acid;

allowing the acetic acid to react with the excess liquid ethanol to produce ethyl acetate and water; and removing ethyl acetate and water.

2. A process according to claim 1, wherein the metallic oxidation catalyst is supported on a hydrophobic carrier.

3. A process according to claim 1, wherein the acetic acid and ethanol are reacted in the presence of an acid ion exchange resin.

4. A process according to claim 2, wherein the acetic acid and ethanol are reacted in the presence of an acid ion exchange resin.

5. A process according to claim 1, wherein the oxygen is provided as air.

6. A process according to claim 2, wherein the oxygen is provided as air.

7. A process according to claim 1, wherein the metallic oxidation catalyst is a nobel metal catalyst.

8. A process according to claim 2, wherein the metallic oxidation catalyst is a nobel metal catalyst.

9. As process according to claim 1 wherein the metallic oxidation catalyst is a Group VIII metal catalyst.

10. As process according to claim 2 wherein the metallic oxidation catalyst is a Group VIII metal catalyst.

11. A process according to claim 1, wherein the metallic oxidation catalyst and the ion exchange resin are mixed together whereby the oxidation and esterification reactions proceed in parallel.

12. A process according to claim 2, wherein the metallic oxidation catalyst and the ion exchange resin are mixed together whereby the oxidation and esterification reactions proceed in parallel.

13. A process according to claim 1, wherein the metallic oxidation catalyst and the ion exchange resin are provided in separate zones whereby the oxidation and esterification reactions proceed sequentially.

14. A process according to claim 2, wherein the metallic oxidation catalyst and the ion exchange resin are provided in separate zones whereby the oxidation and esterification reactions proceed sequentially.

15. A process according to claim 7 wherein the noble metal is provided in the oxidized state.

16. A process according to claim 9 wherein the Group VIII metal is provided in the oxidated state.

17. A process according to claim 1 wherein the metallic oxidation catalyst is a Pd catalyst.

18. A process according to claim 2 wherein the metallic oxidation catalyst is a Pd catalyst.

* * * * *